United States Patent [19]

Swerdloff et al.

[11] Patent Number: 5,625,663
[45] Date of Patent: Apr. 29, 1997

[54] DYNAMIC BEAM FLATTENING APPARATUS FOR RADIATION THERAPY

[75] Inventors: Stuart Swerdloff; Thomas R. Mackie; Timothy Holmes, all of Madison, Wis.

[73] Assignee: Wisconsin Alumni Research Foundation, Madison, Wis.

[21] Appl. No.: 514,366

[22] Filed: Aug. 11, 1995

Related U.S. Application Data

[63] Continuation of Ser. No. 353,749, Feb. 9, 1995, abandoned, which is a continuation of Ser. No. 74,192, Jun. 9, 1993, abandoned, which is a continuation-in-part of Ser. No. 854,521, Mar. 19, 1992, Pat. No. 5,317,616.

[51] Int. Cl.$^6$ ........................................ A61N 5/10
[52] U.S. Cl. ................................. 378/65; 378/113
[58] Field of Search ............................. 378/65, 113

[56] References Cited

U.S. PATENT DOCUMENTS

| | | | |
|---|---|---|---|
| 4,868,843 | 9/1989 | Nunan | 378/65 |
| 5,153,900 | 10/1992 | Nomikos et al. | 378/65 |
| 5,216,255 | 6/1993 | Weldlich | 250/492.3 |

*Primary Examiner*—Craig E. Church
*Attorney, Agent, or Firm*—Quarles & Brady

[57] ABSTRACT

The note path of a banknote validator has a U-shaped transverse cross section. A transverse strip of the note path is illuminated by light from a light transmitting station by means of a unitary light guide which has an arcuate portion conforming to the transverse cross section of the note path. Light reflected from a banknote within the note path, is captured by the light guide and guided to a light receiving station. The light guide is shaded such that a transverse strip of the note path is substantially evenly illuminated. The U-shape of the note path also assists the insertion of notes into the validator, as an inserted note is used to bow during insertion thereby increasing its rigidity.

5 Claims, 11 Drawing Sheets

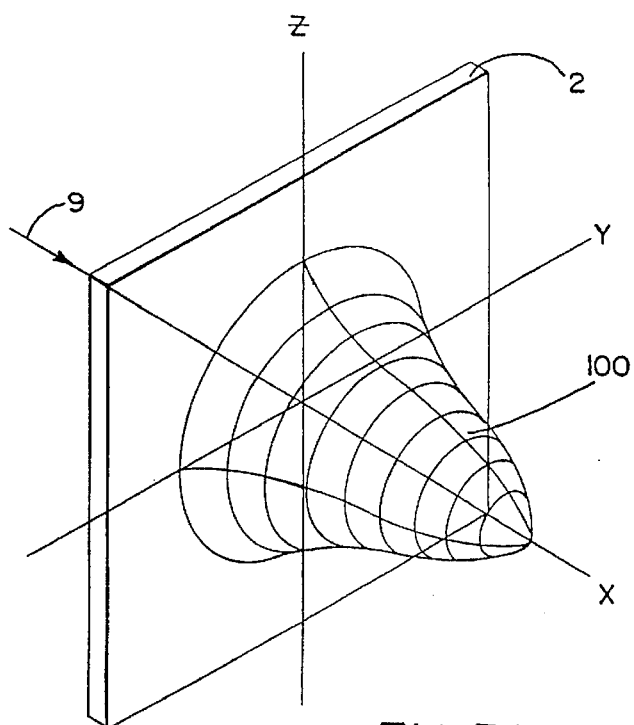
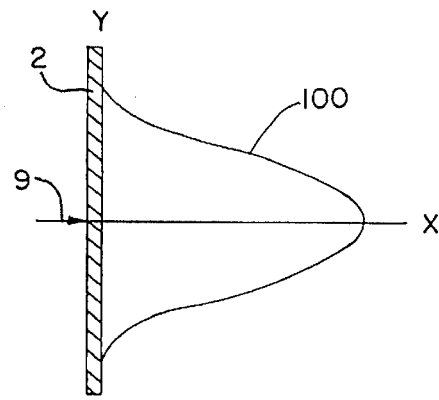
FIG. 3B
PRIOR ART
FIG. 3A
PRIOR ART
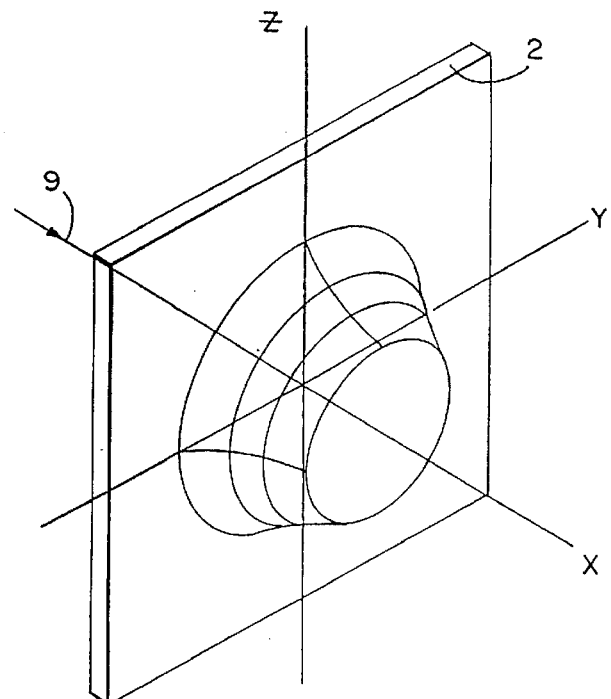
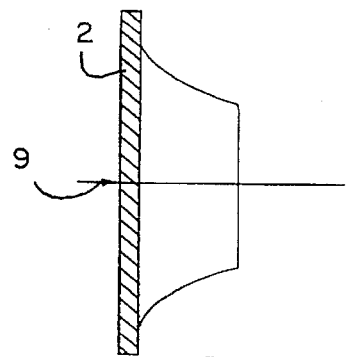
FIG. 3D
PRIOR ART
FIG. 3C
PRIOR ART

DYNAMIC BEAM FLATTENING APPARATUS FOR RADIATION THERAPY

This invention was made with United Stated Government support awarded by the National Institute of Health (NIH), grant Nos, NCI R29 CA48902 and NIH Training Grant NRSA CA09206. The United States Government has certain rights in this invention.

This is a continuation of application Ser. No. 08/353,749 filed Feb. 9, 1995 now abandoned, which is a continuation of application Ser. No. 08/074,192 filed Jun. 9, 1993, now abandoned, which is a continuation of application Ser. No. 07/854,521 filed Mar. 19, 1992 now U.S. Pat. No. 5,317,616.

FIELD OF THE INVENTION

This invention relates generally to radiation therapy equipment for the treatment of tumors, or the like, and specifically to a method and apparatus for accommodating uneven fluence within a radiation beam.

DESCRIPTION OF THE ART

Medical equipment for radiation therapy treats tumorous tissue with high energy radiation. The radiation dose and the placement of the dose must be accurately controlled to insure both that the tumor receives sufficient radiation to be destroyed, and that damage to the surrounding and adjacent non-tumorous tissue is minimized.

One radiation source employed in radiation therapy is a linear accelerator (linac). A linear accelerator consists of a series of metal electrodes spaced along an evacuated straight path. Every other electrode is connected together to one terminal of a high frequency electric generator, and the intervening electrodes are connected to the opposite terminal of the generator to produce an alternating electric field which accelerates electrons from an electron source. Effectively, an electromagnetic wave is set up that travels continuously through the evacuated chamber and electrons "ride" the electromagnetic wave.

Referring to FIG. 3(a), the electrons accelerated by the linear accelerator are directed at a target 2. When electrons strike one side of the target 2 and pass through or near the electric field of a target atom they lose some energy. Some of the energy lost by an electron may appear as a radiation photon having a specific quantum of energy. After each energy loss the electrons are typically deflected in a new direction and may experience several additional decelerations before finally stopping. Each deceleration generates radiation photons of widely different energies. The resulting radiation emitted from the target thus has a continuous spectrum of energies ranging from zero to the maximum kinetic energy of the electrons entering the target 2.

The process of slowing an electron and emitting a photon is called bremsstrahlung or bremssradiation, a German word meaning breaking radiation because it is associated with a slowing of the electrons. The greater the initial velocity of the electron and the closer the electron approaches the nucleus, the more kinetic energy will be transferred to the bremsstrahlung (i.e. the higher the energy of the emitted photon).

Again referring to FIG. 3(a), the linac directs the electron beam toward one locus on a target and, a relatively large radiation fluence emanates from the opposite side of the target 2 along a central ray 28 concentric with the electron beam. Subsequent electron collisions are normally not along this central ray 28 and therefore x-ray flux from later collisions is emitted from the target at angles removed from the central ray 28. The net effect is that photons emanate from the target at different angles relative to the central ray 28, a proportionally larger number emanating along the central ray and a lesser number at angles diverging about this ray 28. A non-uniform radiation fluence profile 100 results.

The radiation beam does not emanate from a single point on the target but rather from an "emitting area" of the target. As a result, the non-uniformity of the fluence profile emanating from the target is accentuated when the beam is collimated. In such collimation a central portion of the beam is produced in the space traversed by radiation emanating from all parts of the emitting area. An outer penumbra is produced in the space traversed by radiation emanating from only part of the emitting area, (i.e. radiation passing through the collimator at a relatively sharp angle). The penumbra has less fluence.

The combined effect of the penumbra and the fluence profile is that the variation of fluence across the beam field is more extreme.

Radiation therapy planning techniques generally assume that the fluence of the radiation source is uniform throughout the cross section of the radiation beam. However, as noted above with respect to linacs, most sources of radiation produce beams with greater fluence toward their centers. Accordingly, it is typical to use a beam flattening filter, thicker toward the center, to render the fluence profile of the beam more uniform.

Referring to FIG. 3(b), a beam-flattening filter constructed of a radiation attenuating material is placed directly within a beam to absorb some of the fluence within the central section of a source fluence profile reducing this central section to a fluence comparable to the fluence at the edges of the beam. In this manner, the beam fluence can be controlled and made more uniform.

A drawback to beam flattening filters is that they waste radiation energy, reducing the intensity of the beam they filter. Therapy sessions with reduced beam intensities require longer irradiation sessions to deliver desired irradiation doses to a tumor site and hence limit therapy throughput rates.

In addition, beam flattening filters also remove low energy photons from the center of the beam and allow them to pass around the periphery. This effect is called beam hardening and results in a non-uniform energy spectrum within the beam.

Further, flattening filters cannot compensate for non-uniformities that evolve with time and use. Therefore, therapy planning that relies on assumptions of uniform fluence in the radiation beam may be inaccurate.

SUMMARY OF THE INVENTION

The present invention is a method of correcting for non-uniform fluence profiles in a radiation source used for radiation therapy that minimizes the amount of wasted radiation energy.

In one embodiment, a dose calculator receives both a desired fluence profile for the patient and a non-uniform source fluence profile and generates an attenuation profile in accordance with the desired fluence profile such that the attenuation profile corrects for the non-uniformity of the non-uniform source profile. A compensator receives the desired dose profile and attenuates the non-uniform source fluence profile to produce the desired fluence profile.

It is thus one object of the invention to provide a simple and reliable means for producing a desired fluence profile from a radiation source having an arbitrary non-uniform source profile. The control signal for the compensator may be adjusted to account for non-uniform radiation source profiles, using that non-uniformity if it comports with the desired profile and modifying it only as necessary in other cases. Thus, there is no unnecessary attenuation as might be produced by a static beam flattening filter.

The compensator may include a number of radiation attenuating leaves in a rack positioned within a radiation beam before it enters a patient. The leaves may move into the radiation beam in a closed state (each leaf thus occluding one ray of the beam) and move out of the radiation beam in an open state to allow unobstructed passage of the associated ray.

A motivation mechanism allows the leaves to be independently moved between the open and closed states and a timer communicating with the motivation mechanism controls the ratio of the period of time during which each leaf is in the closed state to the period in which each leaf is in the open state to control the average intensity of each ray of the beam.

It is another object of the invention to provide a method of attenuating the individual rays of a high energy radiation beam with negligible affect on the spectrum of the radiation. In contrast, static beam flattening filters attenuate low energy photons yet pass high energy photons resulting in "beam hardening". The leaves of the compensator do not attenuate but provide nearly complete blockage or complete passage without affecting spectral composition.

It is yet another object of the invention to provide a therapy apparatus that facilitates short irradiation sessions. By minimally limiting ray intensity and eliminating a static flattening filter, relatively large irradiation doses may be directed toward a tumor site in a reduced period of time. Short irradiation sessions mean minimal patient discomfort and greater throughput rate for each radiation therapy machine.

In a second embodiment, a flat beam is produced by oscillating the electron stream of the linac at a constant velocity so that the electron stream strikes a radiation producing target at different points along an impact line rather than at one point. By oscillating the electron stream, the source fluence profile is "smeared" over the beam width producing a beam that, although instantaneously non-uniform, has an average uniformity over time within the plane of oscillation.

The second embodiment may include a linac with an electromagnet capable of deflecting an electron stream along a plane of oscillation as it passes through the electromagnet. By reciprocating the electron stream along an impact line on the target, the resulting field on the opposite side of the target has an average uniform intensity along the plane of oscillation. Again, as with the first embodiment, there is no "beam hardening" (i.e. each ray of the average uniform profile has the same spectrum of photons).

Importantly, with this second embodiment, small discrepancies in the source profile along the plane of oscillation due to either design/defect or worn hardware are unimportant. The oscillating source profile effectively compensates for such discrepancies by averaging the fluence variations over the plane of oscillation. For therapy planning purposes, when the second embodiment of the compensator is employed to produce an average uniform profile, the precise source profile of the radiation source need no longer be known. It is sufficient, for therapy planning purposes, that the average fluence across the oscillation plane is known.

The foregoing and other objects and advantages of the invention will appear from the following description. In the description, reference is made to the accompanying drawings which form a part hereof and in which there is shown by way of illustration several preferred embodiments of the invention. Such embodiments do not necessarily represent the full scope of the invention, however, and reference must be made therefore to the claims herein for interpreting the scope of the invention.

BRIEF DESCRIPTION OF THE DRAWINGS

FIGS. 3(a)–3(d) are graphical representations of a radiation source fluence profile where FIG. 3(a) and 3(b) show a three and two dimensional uncompensated beam fluence profile, respectively, and FIG. 3(c) and 3(d) shows the effects of a beam flattening filter, in three and two dimensions respectively;

FIG. 15(a) is a non-uniform source profile and FIG. 15(b) is a desired profile;

DETAILED DESCRIPTION OF THE PREFERRED EMBODIMENT

Figure 1:
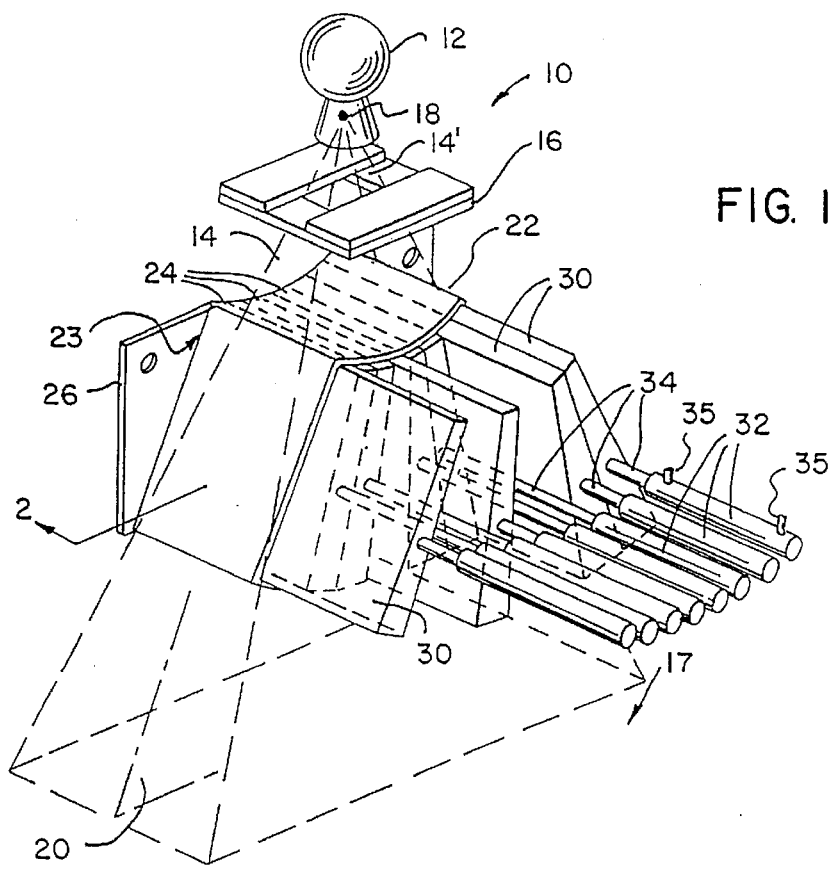
FIG. 1 is a perspective view of the compensator assembly used in the present invention positioned within a fan beam of radiation, showing the compensator leaves and their associated pneumatic cylinders.

Referring to FIG. 1, a radiation therapy unit 10 suitable for use with the present invention includes a radiation source 12 producing a generally conical radiation beam 14' emanating from a focal spot 18 and directed towards a patient 17 (not shown in FIG. 1). The conical beam 14' is collimated by a radiation opaque mask 16 constructed of a set of rectangular collimator blades to form a generally planar fan beam 14 centered about a fan beam plane 20.

I. The Radiation Source

Figure 2:
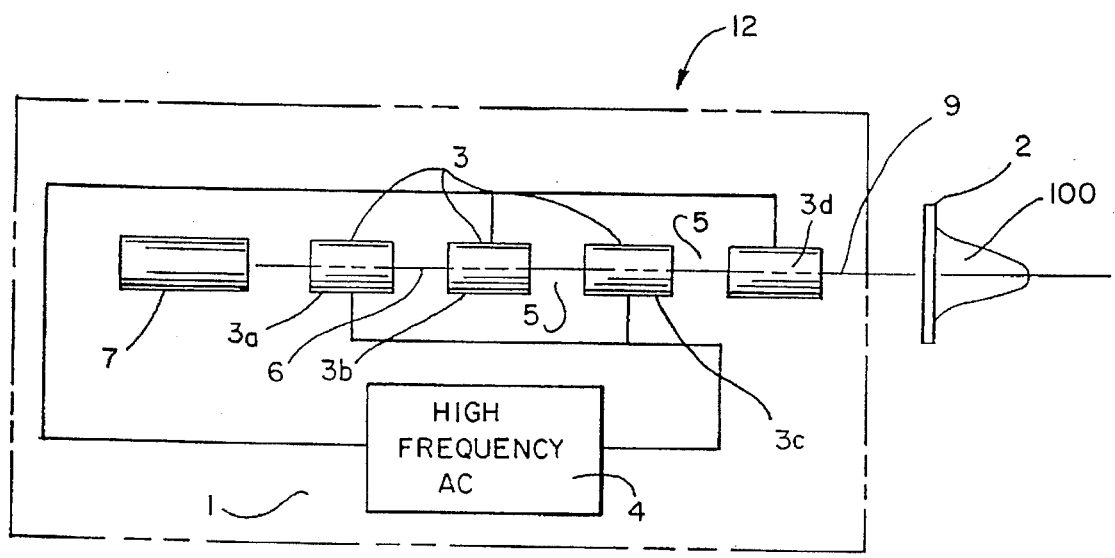
FIG. 2 is a schematic view of a radiation source consisting of a linear accelerator and an accelerator target.

Referring to FIG. 2, the radiation source used in the present invention is a linear accelerator 1 (linac) used in combination with an x-ray producing target 2. The linear accelerator 1 consists of series of metal electrodes 3 spaced along a central axis 9 and enclosed in a vacuum. Alternate electrodes 3a, 3c are connected to one end of a high frequency alternating current generator 4, and the intervening electrodes 3b, 3d are connected to the opposite end of the generator 4. Adjacent electrodes form multiple radio frequency cavities 5 along the axis 9 and produce fields with the necessary polarization so that electrons 6 between the electrodes 3 will be accelerated along the central axis 9.

During operation, electrons 6 from a source 7 are accelerated to a desired speed and directed at the target 2 as they pass through the radio frequency cavities 5. When the electrons 6 impact one side of the target 2, the impacting electrons 6 lose energy and at the same time produce x-ray photons 8 that emanate from the opposite side of the target 2 along the central axis 9.

All of the electrons 6 impacting the target 2 do not continue along the central axis 9. Some electrons 6 scatter within the target 2. After an electron 6 initially impacts a target atom, the electron 6 loses energy in the form of a photon, and typically changes direction. The electron 6 continues at a lesser velocity after the first impact and then typically impacts a second target atom off the central axis 9 losing additional energy in the form of a second photon which emanates from the target along the line of collision rather than along the central axis 9. Electron-atom collisions continue until the electron 6 loses all of its energy, ideally, within the target.

Figure 16:
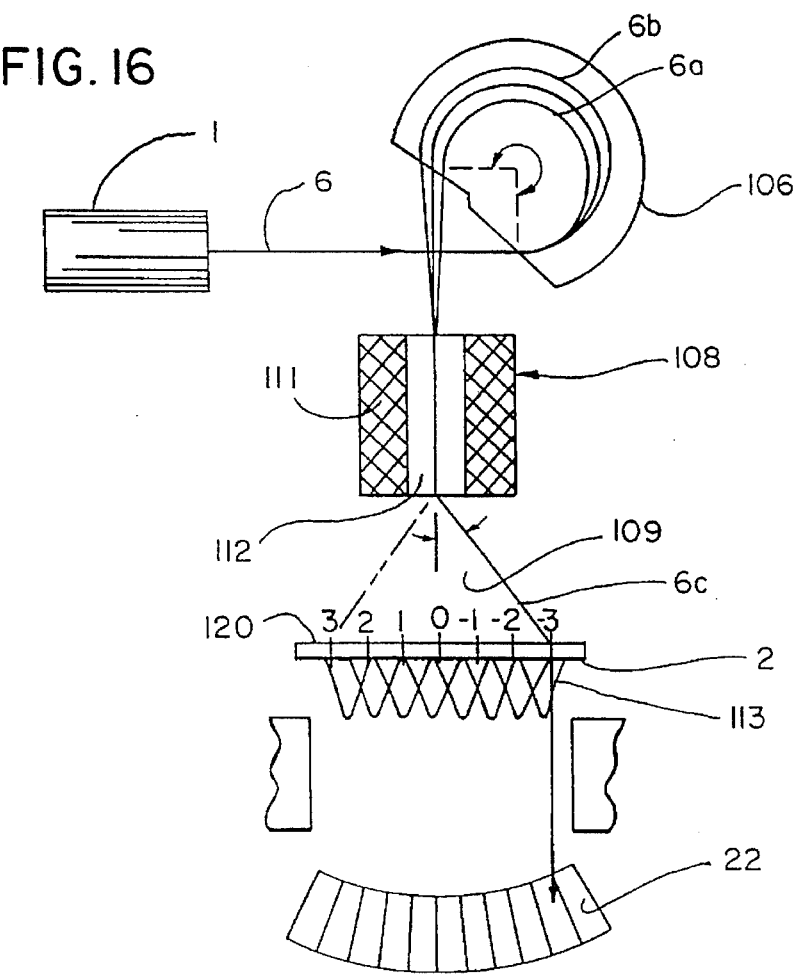
FIG. 16 is a schematic view of a radiation source showing a linac, a deflection yoke, and a target used in a second embodiment and the compensator of the first embodiment.

Many photons emanate from the target 2 in directions diverging about the central axis 9. Thus, as seen in FIG. 3(a), the resulting fluence profile 100 emanating from the target 2 is generally of a bell shape. Referring to FIG. 16, the linac 1 may employ an achromatic bending magnet 106 to facilitate a more compact design. As seen in FIG. 16, by using a bending magnet 106, the actual position of the linac 1 need not be perpendicular to the x-ray target 2, but may be substantially parallel thereto. Employing an achromatic bending magnet, the actual circumferential width of a gantry 44 used with the radiotherapy system can be limited. Thus, the linac-gantry configuration may be employed in a standard sized radiation therapy room.

The magnet 106 provides desirable achromatic focusing properties. Referring to FIG. 16, the lower energy component 6a of the stream is deflected through a loop of small radius and the high energy component 6b is deflected through a loop of larger radius. The important property of the achromatic magnet is that these components 6a, 6b are brought back together to the same position, angle and beam cross-section at the magnet exit, as they were when they left the linac 1.

II. The Compensator

Referring again to FIG. 1, a compensator 22 is centered in the fan beam 14 and about a fan beam plane 20, prior to the radiation being received by a patient (not shown in FIG. 1), and includes a plurality of adjacent trapezoidal leaves 30 which together form an arc of constant radius about the focal spot 18. The leaves 30 are held in sleeves 24. The sleeves 24 are constructed of radio translucent materials and attached at their inner ends 23 to a mounting plate 26 which is fixed relative to the focal spot 18. The mounting plate 26 is constructed of a sturdy, possibly radiopaque material and is positioned just outside the fan beam 14 to prevent interference with the fan beam 14.

Figure 4:
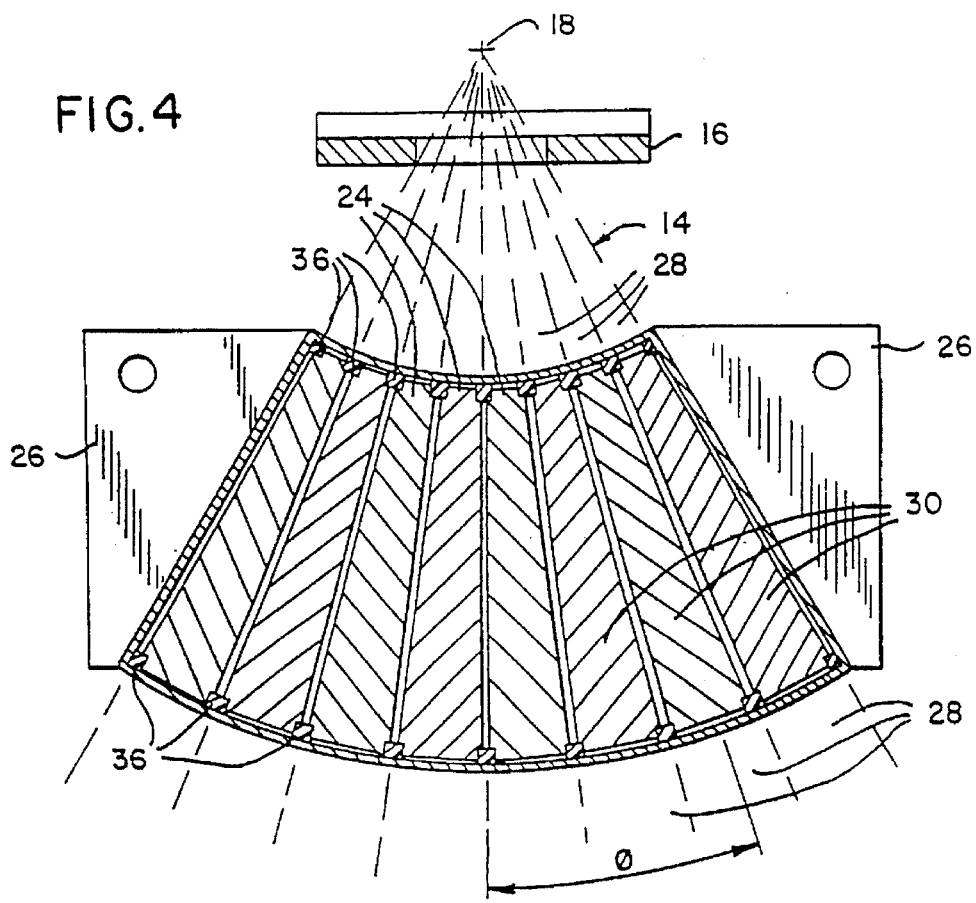
FIG. 4 is a cross-section of the compensator assembly of FIG. 1 along line 4—4 showing the trapezoidal aspect of each compensator leaf, the fan beam of radiation, and the guide rails for supporting the compensator leaves when they move.
Figure 5:
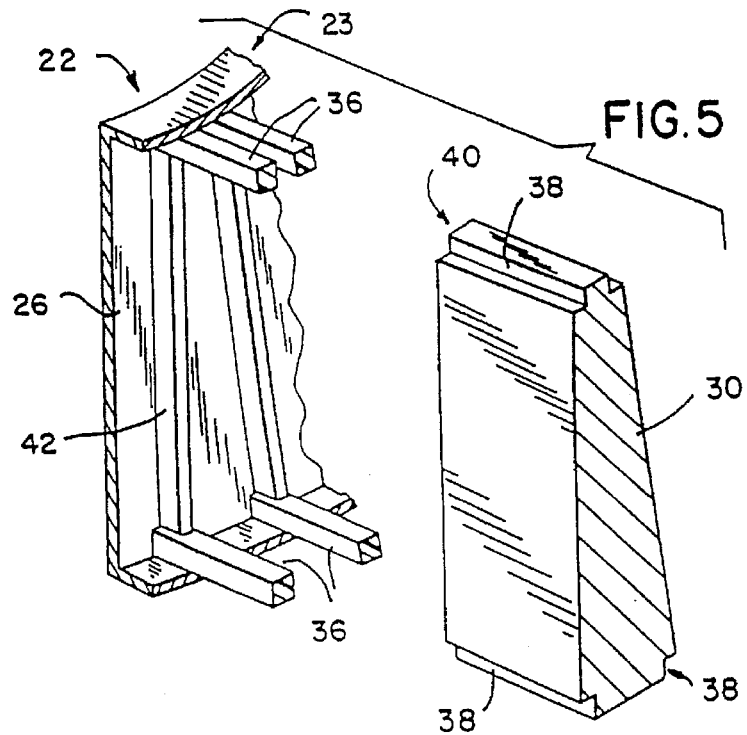
FIG. 5 is a cutaway perspective view of a set of guide rails and one leaf of FIG. 4 showing a collar for supporting the leaf in its fully closed position.

Preferably, the leaves 30 of the compensator 22 subtend the entire fan beam 14 to divide the fan beam 14 into a set of adjacent slab-like rays 28 at offset angles $\phi$. Referring to FIGS. 4 and 5, each sleeve 24 is open at its outer end 27 to receive, by sliding, a comparably sized trapezoidal leaf 30 constructed of a dense, radiopaque material such as lead, tungsten, cerium, tantalum or a related alloys.

Each leaf 30 may slide completely within its corresponding sleeve 24 to block the ray 28 associated with that sleeve 24. When the leaf 30 blocks its corresponding ray 28, it is referred to as being in a "closed state". The sleeves 24 are of ample length to permit each leaf 30 to slide out of the path of the fan beam 14, so as to leave its corresponding ray 28 completely unobstructed, and yet to still be guided by the sleeve 24. In this non-blocking position, a leaf is referred to as being in the "open state".

Each leaf 30 may be moved between its open and closed states by means of a corresponding pneumatic cylinder connected to the leaf 30 by a flexible link 34. The pneumatic cylinders 32 have internal pistons (not shown) that may be moved at high velocity between the ends of the cylinders 32 by means of pressurized air coupled to the cylinders 32 through supply hoses 35. The supply hoses 35 are fed by a compensator control (not shown in FIGS. 1 or 4) to be described below. The pneumatic cylinders 32 are capable of applying high forces to the leaves 30 to move them rapidly and independently between the open and closed states.

Referring now to FIGS. 4 and 5, the leaves 30 are supported and guided within the sleeves 24 by guide rails 36 fitted into notches 38 cut along the edges of the leaves 30. The notches 38 allow the guide rails 36 to slidably retain the leaves 30 within the sleeves 24 during motion between the open and closed states.

In the closed state, the inner end 40 of each leaf 30 is captured by a rigid collar 42 attached to the mounting plate, which aligns the leaf 30, more accurately than may be done by the guide rails 36, with the mounting plate 26 and hence with the fan beam 14. Whereas the guide rails 36, which are ideally radio translucent, are relatively insubstantial, in contrast, the collar 42, positioned outside the fan beam 14 on the mounting plate 26, need not be radio-translucent and hence is more substantial in construction. A collar (not shown) similar to collar 42, supports each leaf 30 when it is fully in the open state. Because the leaves 30 spend most of their time fully in the open or closed states, they are, at most times, firmly located by a supporting collar 4.

A. Radiation Therapy Hardware of the First Embodiment

Figure 6:
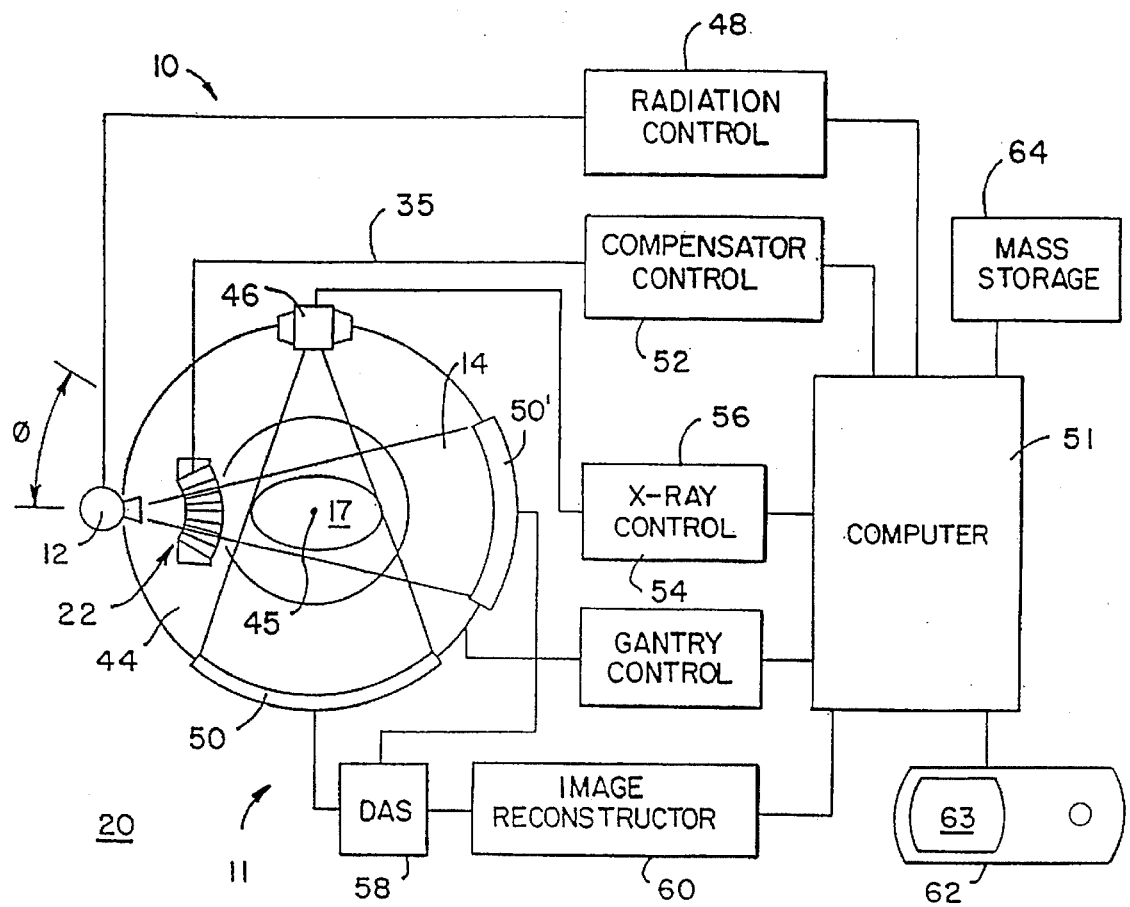
FIG. 6 is a block diagram showing the elements of a radiation therapy apparatus incorporating a computer controller compensator used in the first embodiment of the present invention.

Referring now to FIG. 6, the radiation source 12 is mounted on a gantry 44, the latter rotating within the fan beam plane 20 about a center of rotation 45 in the patient 17 so that the fan beam 14 may irradiate a slice of the patient 17 from a variety of gantry angles θ.

The radiation source 12 is controlled by a radiation control module 48 which turns the radiation beam 14 on or off under the control of a computer 51.

A compensator control module 52 provides a source of compressed air and valves to gate that air through supply hoses 35 to control, separately, the pneumatic cylinders 32 to move each of the leaves 30 in and out of its corresponding sleeve 24 and ray 28 (see also FIG. 1). The compensator control module 52 also connects with computer 51 to allow program control of the compensator 22 to be described.

An exit detector 50' positioned on the gantry 44 opposite the radiation source 12 measures the radiation passing through the patient 17 and is connected to a Data Acquisition System 58 as will be described below. Preferably, the exit detector 50' is comprised of a plurality of detector elements each subtending the same angle as one leaf of the compensator 22.

The compensator control module 52, moves the leaves 30 of the compensator 22 rapidly between their open and closed states to either fully attenuate or to provide no attenuation to each ray 28. The ratio between the closed and open states, or the "duty cycle" for each leaf 30, affects the total energy passed by a given leaf 30 at each gantry angle and thus controls the average fluence of each ray 28. The ability to control the average fluence at each gantry angle permits accurate control of the dose provided by the radiation beam 14 through the irradiated volume of the patient 17 by therapy planning methods to be described below.

A tomographic imaging system 11 employing an x-ray source 46 and an opposed detector array 50 may be advantageously mounted on the same gantry 44 as the radiation source 12 to produce a tomographic or slice image of the irradiated slice of the patient 17 prior to radiation therapy for planning purposes.

A gantry control module 54 provides the signals necessary to rotate the gantry 44 and change the angle θ of the fan beam 14, hence to change the position of the radiation source 12, exit detector 50', computed tomography x-ray source 46 and detector array 50. Gantry control module 54 connects with computer 51 so that the gantry may be rotated under computer control and also to provide the computer 51 with a signal indicating the gantry angle θ to assist in that control.

Control modules for the tomographic imaging system 11 include: x-ray control module 56 for turning on and off the x-ray source 46, and data acquisition system 58 for receiving data from the detector array 50 in order to construct a tomographic image.

An image reconstructor 60 typically comprising a high speed array processor or the like receives the data from the data acquisition system 58 in order to assist in "reconstructing" a tomographic image from such data according to methods well known in the art. The image reconstructor 60 also communicates with computer 51 to assist in high speed computations used in the present invention as will be described below. The tomographic image allows verification of the patient setup just prior to radiation therapy treatment.

A terminal 62 comprising a keyboard and display unit 63 allows an operator to input to programs and data to the computer 51 and to control the radiation therapy and tomographic imaging equipment 10 and 11 and to display tomographic images produced by the image reconstructor 60 on the display 63. A mass storage system 64, being either a magnetic disk unit or tape drive, allows the storage of data collected by the tomographic imaging system 11 for later use.

Computer programs for operating the radiation therapy system 10 will generally be stored in mass storage unit 64 and loaded into the internal memory of the computer 51 for rapid processing during use of the system 10.

B. Operation of the Therapy Equipment

Prior to a radiation therapy session, the radiation source 12 and exit detector 50' can be used to identify the source fluence profile 100 (source profile) of the particular radiation source 12 (see FIG. 3(a)). The radiation source 12 may direct a beam toward the exit detector 50' with no intervening patient 17. The source profile 100 can be obtained and divided into separate beam rays 28 so that a discrete fluence value can be associated with each leaf 30 of the compensator 22.

Figure 7:
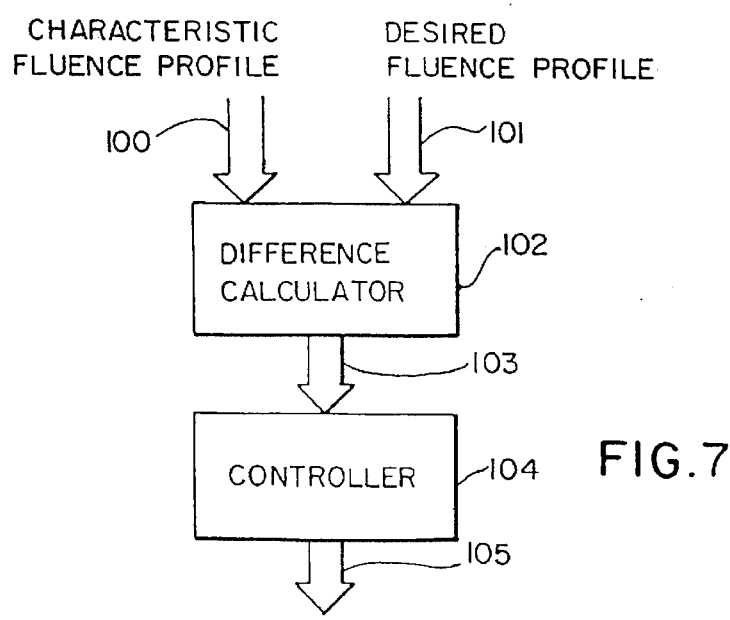
FIG. 7 is a block diagram depicting a difference calculator which compares a source fluence profile and a desired fluence profile and generates an attenuation signal.

Referring to FIG. 7, once the source profile 100 is obtained, a dose calculator 102 effectively compares the source profile 100 to a desired fluence profiles 101 (desired profile) to be directed at a patient for every gantry angle 8. The dose calculator 102 generates duty cycles 103 indicating the ratio of time each leaf 30 should be in the closed state to the time each leaf 30 should be in the open state to attenuate the source profile 100 and produce the desired profile 101.

Using the duty cycles 103, a controller 104 takes into account the non-uniform source profile 100 and generates an attenuation profile 105 corresponding to each desired profile 101. The attenuation profiles 105 control the movement of compensator leaves 30 at every gantry angle θ. The attenuation profiles 105 directed at an arbitrary slice of the tumor make up a treatment sinogram for a particular tumor slice.

The attenuation profiles 105 needed to generate the treatment sinograms are determined by therapy planning software (described below) and stored in the computer 51.

C. Therapy Planning Software

The generation of a treatment sinogram needed to obtain the full benefits of the above described compensator is performed by specially developed software running on the computer 51 and reconstructor 60. Although the treatment planning is performed in software, it will be recognized that the planning may also be implemented in discrete electronic circuitry dedicated to this operation and that such dedicated circuitry may be employed to provide even greater speed to this process.

Figure 8A:
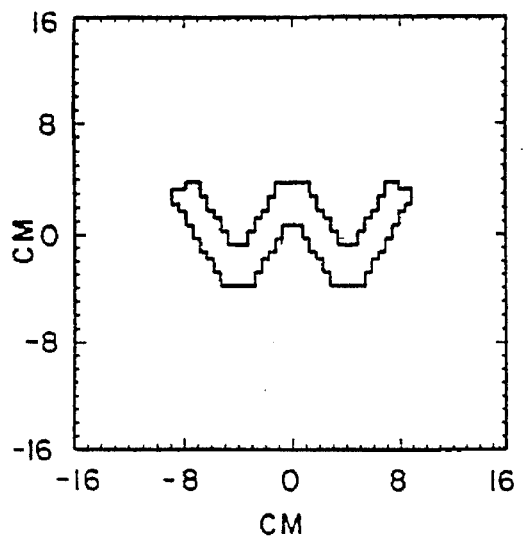
FIGS. 8(a)–(d) are dose distributions of a hypothetical tumorous region showing dose intensity by lines of equal dose, with FIG. 8(a) showing a desired dose distribution and FIGS. 8(b), (c), and (d) showing progressive actual dose distributions after two, three and ten iterations of a radiation planning procedure used with the present invention.
Figure 8B:
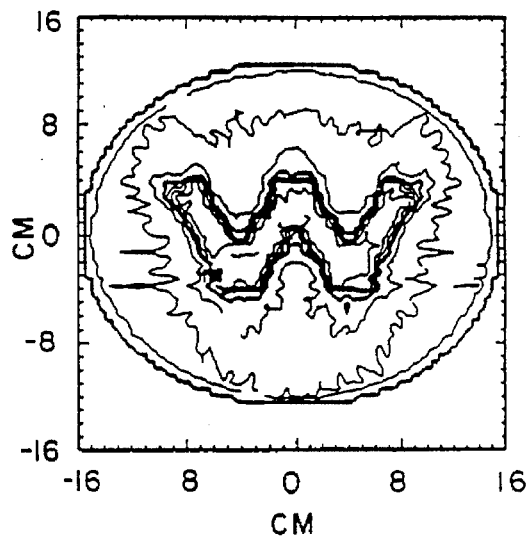

Referring to FIG. 8(a), the generation of the desired treatment sinogram to control compensator 22 begins with the definition of a desired dose map 66. A typical desired dose map 66 assigns a relatively high radiation dose, within a dose constraint, to an area of tumorous tissue 68 and a second lower radiation dose to the area of healthy tissue 70 outside of that region. The healthy tissue 70 may include an area 72 including a radiation sensitive organ or the like to which an even lower radiation dose may be assigned.

The desired dose map 66 is stored within the memory of computer 51 as an array of elements each element holding one digital value, and may be most easily entered by displaying the tomographic view of the slice of patient 17 on the display 63 of the terminal 62 and manually tracing around the tumorous area 68 using of a track-ball or similar input device as is well understood in the art. Standard area-filling computer programs may be used to transfer the dose values assigned to each traced region to the appropriate element in the array of memory representing the desired dose map 66.

Figure 9:
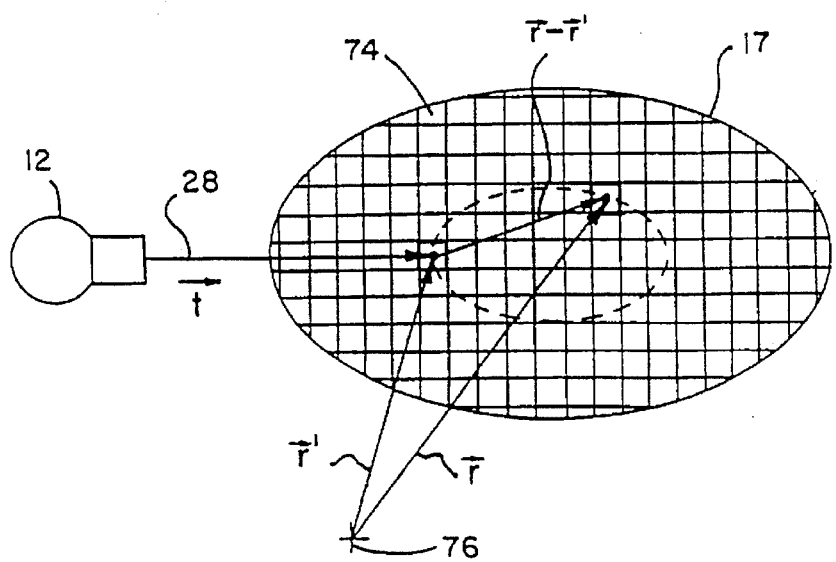
FIG. 9 is a diagrammatic representation of a patient receiving radiation therapy, showing the scatter kernel and the coordinate system used to describe radiation planning used with the present invention.

Each element of the dose map 66 thus defines the dose desired at each of the plurality of volume elements 74 ("voxels") within a slice of the patient 17. Referring to FIG. 9, each voxel 74 of the patient 17 may be identified by a vector $\vec{r}$ defined from a given reference point 76. The dose at each voxel 74 is $D(\vec{r})$.

1. Converting Dose to Terma a. Terma

Generally, the dose at any voxel $\vec{r}$ will depend on the energy received at that voxel $\vec{r}$ from radiation scattered from adjacent voxels $\vec{r}^1$ (where adjacent voxels $\vec{r}^1$ include the voxel $\vec{r}$, i.e., the radiation received directly from the radiation source 12). The dose $D(\vec{r})$ for a given voxel $\vec{r}$ is given by the following formula:

$$D(\vec{r}) = \int T(\vec{r}^1) A(\vec{r}-\vec{r}^1) d^3\vec{r}^1 \tag{1}$$

where $T(\vec{r}^1)$ is a value indicating the magnitude of the primary total energy released from $\vec{r}^1$ per unit mass of that voxel $\vec{r}^1$ and is called the "terma" (total energy released per unit mass).

For a monoenergetic external radiation source, the terma rate $\dot{T}(\vec{r})$ is described by:

$$\dot{T}(\vec{r}) = \mu/\rho(\vec{r}) E \dot{\phi}(\vec{r}^1) dt \tag{2}$$

where $\mu/\rho$ is an effective mass attenuation value at the voxel $\vec{r}^1$, E is the energy of the radiation photons in Joules, $\dot{\phi}$ is the distribution of the fluence rate (flux density). The integration of energy times fluence rate over time is energy fluence $\Psi(\vec{r}^1)$ where:

$$\Psi(\vec{r}^1) = E \int \phi(\vec{r}^1) dt \tag{3}$$

hence $$T(\vec{r}^1) = \mu/\rho(\vec{r}^1) \Psi(\vec{r}^1) \tag{4}$$

Equation (4) basically relates how much energy from the ray 28 interacts with the voxel r'.

b. Convolution Kernel $A(\vec{r}-\vec{r}^1)$ is a convolution kernel describing non-stochastic energy transport or scatterin g in a uniform medium. $A(\vec{r}-\vec{r}^1)$ thus describes how the energy from each voxel $\vec{r}^1$ spreads to contribute to the dose at voxel $\vec{r}^1$.

The kernel $A(\vec{r}-\vec{r}^1)$ may be generated using a Monte Carlo method as is generally understood in the art. As mentioned, it is a three-dimensional function indicating the fraction of energy absorbed at voxel $\vec{r}$ per unit of energy released at voxel $\vec{r}^1$. The energy emitted from the terma of each voxel $\vec{r}^1$ finds it source in a directed ray 28 from external radiation source 12 and thus $A(\vec{r}-\vec{r}^1)$ is generally anisotropic as suggested in FIG. 10, spreading outward away from the entry of ray 28. Energy conservation requires that:

$$\int A(\vec{r}^1) d^3\vec{r}^1 = 1.0 \tag{5}$$

That is, if the energy transferred by the primary interaction were all deposited on the interaction point, the kernel would be approximated as a delta function.

Figure 10:
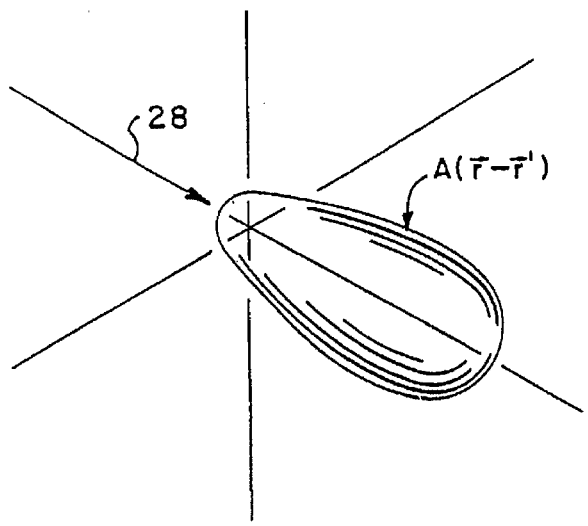
FIG. 10 is a perspective representation of a monodirectional scatter kernel associated with a radiation beam at one gantry angle.

Referring still to FIG. 10, the anisotropy of $A(\vec{r}-\vec{r}^1)$ is related to the gantry angle $\theta$ and thus of the angle of incidence of the ray 28 at $\vec{r}^1$. If the gantry angles $\theta$ at which the patient 17 is irradiated are predetermined, a multidirection convolution kernel $B(\vec{r}-\vec{r}^1)$ shown in FIG. 8, may be created from weighted superimposition of the kernels $A(\vec{r}-\vec{r}^1)$.

Figure 11:
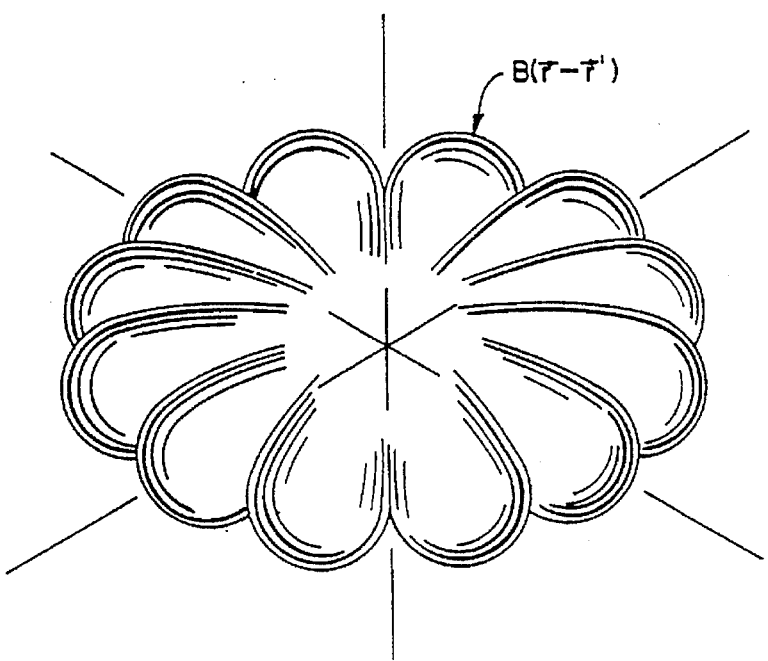
FIG. 11 is a perspective representation of a composite multidirectional scatter kernel associated with a plurality of radiation beams at multiple gantry angles.

Referring to FIG. 11, assuming that the spreading of radiation is approximately equal for all beam directions and the rays 28 from each gantry angle $\theta$ contribute equally to the terma at voxel $\vec{r}^1$, then the multidirectional convolution kernel reduces to a "isotropic" form as follows:

$$B(\vec{r}-\vec{r}^1) = \frac{1}{n} \sum_{i=1}^{n} A(\vec{r}-\vec{r}^1)_i \tag{6}$$

where n is the number of discrete gantry angles from which rays 28 are projected.

For multiple rays 28 at different gantry angles, the total dose at a given voxel $\vec{r}$ is the sum of doses from each constituent beam is therefore:

$$D(\vec{r}) = \int T(\vec{r}^1) B(\vec{r}-\vec{r}^1) d^3\vec{r}^1 \tag{7}$$

where $T(\vec{r}^1) = nT(\vec{r}^1)_i$ the latter term being the contributed portion of the terma for the ith gantry angle.

This simplification assumes that the contribution to the terma from each ray 28 is equivalent and takes advantage of the distributive property of convolution. Errors in this assumption are reduced by the filtration to be discussed later.

Equation (7) substantially simplifies the calculation of dose from terma but still requires a convolution for each voxel $\vec{r}$ times the total number of voxels $\vec{r}^1$ to calculate the dose over the entire patient volume. Preferably, therefore, the calculational efficiency of the fast Fourier transform can be used and equation (7) converted to the following:

$$D(\vec{r}) = F^{-1}\{F\{T(\vec{r}^1)\} \cdot F\{B(\vec{r}-\vec{r}^1)\}\} \tag{8}$$

where F and $F^{-1}$ symbolize Fourier and inverse Fourier transforms respectively. This simplification of equation (8) requires that the kernel $B(\vec{r}-\vec{r}^1)$ be spatially invariant and relies on the convolution theorem which states that convolution of two spatially invariant quantities in a space domain is equivalent to multiplication in the frequency domain.

The assumption of the spatial invariance of $B(\vec{r}-\vec{r}^1)$ is correct only to a first order approximation. Typically, the kernel $B(\vec{r}-\vec{r}^1)$ for an external radiation source 12 is a complex function of: (1) beam hardening of a polyenergetic x-ray beam (i.e., the effect of the filtration of the patient 17 in increasing the proportion of high frequency or high energy radiation components), (2) the number of rays 28 crossing each voxel, and (3) exponential attenuation by the patient mass.

In the preferred embodiment, this first factor, beam hardening, is neglected because it is an effect smaller than the attenuation problem. Thus, the photon energy spectrum in the patient 17 may be assumed to be the same as that of the external radiation source 12. This simplification is not required, however, and it will be understood that beam hardening could be accurately accounted for by representing a photon energy spectrum by a finite number of separately convolved energy intervals.

The second factor, the difference in the number and orientation of rays 28 that cross each voxel, caused by the geometry of a finite number of gantry angles and the fan orientation of the beam 14, affect spatial invariance. Problems arising from the fan orientation of the beam (in contrast to a parallel beam geometry) are largely solved if there is a full rotation of the gantry 44. Errors resulting from the fact that irradiation is performed at only a finite number of gantry angles have been determined to be acceptable.

The third factor affecting the assumption of spatial invariance is the attenuation of the medium. This affects the fractional contribution of the total terma from the beams at each gantry angle. Accordingly, in those steps of the planning procedure, as will be noted below, where accurate calculation of dose is critical, the dose distribution is calculated separately for each beam based on the attenuation of overlying voxels, such attenuation deduced from the parameters of the tomographic image. In this case the simplification of equation (8) may not be employed and repeated convolutions must be performed. In certain steps in the planning process, however, as will be noted, an estimate is sufficient and in these cases $B(\vec{r}-\vec{r}^1)$ is assumed to be spatially invariant and the dose calculated according to equation (8).

Production of terma values from a desired dose map 66 is then simply the process of inverting equation (8) as follows:

$$T(\vec{r}^1) = F^{-1}\left\{ \frac{F\{D(\vec{r})\}}{F\{B(\vec{r}-\vec{r}^1)\}} \right\} \quad (9)$$

This inversion requires that there be no significant "zeros" (typically at high frequencies) in the denominator term $F\{B(\vec{r}-\vec{r}^1)\}$ or more simply that the kernel $B(\vec{r}-\vec{r}^1)$ be spatially compact (i.e., the Fourier transform of a spatially compact kernel will have significant high frequency content). It has been determined by the present inventors that the kernels dictated for patients 17 are sufficiently compact to allow this Fourier deconvolution.

Figure 12:
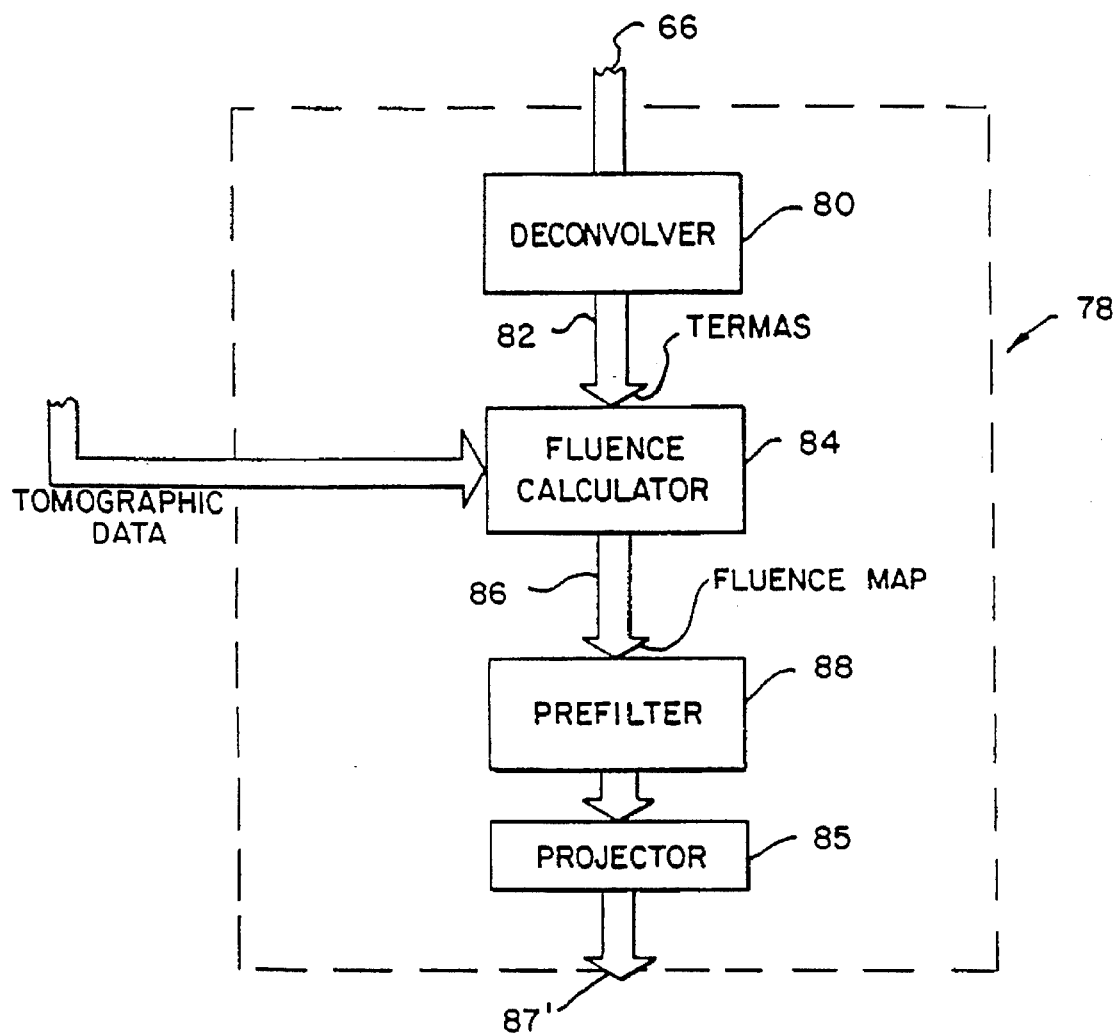
FIG. 12 is a block diagram depicting the fluence profile calculator which takes a desired dose map and calculates a fluence profile.

Referring now to FIG. 12, this deconvolution to produce a terma map 82, giving the terma for each voxel $\vec{r}$, from the desired dose map 66, is represented by process block 80.

2. Converting Terma to Voxel Energy Fluence

Knowing the terma map 82, the energy fluence $\Psi(\vec{r}^1)$, which is a measure of the beam intensity, can be determined at each corresponding voxel by equation (4) from a knowledge of $\mu/\rho$ as follows:

$$\Psi(\vec{r}^1) = \frac{T(\vec{r}^1)}{\frac{\mu}{\rho}(\vec{r}^1)} \quad (10)$$

The value of $\mu/\rho$ may be estimated and considered a constant or actual $\mu/\rho$ may be deduced from the tomographic scan data collected by means of the tomographic imaging system 11, (shown in FIG. 6). In this manner and as illustrated by process block 84 of FIG. 12, a fluence map 86 giving the fluence at each point of the terma map may be determined.

3. Converting Voxel Energy Fluence to Energy Fluence Profile

The energy fluence $\Psi(\vec{r}^1)$ at each voxel $\vec{r}^1$ is related to the energy of the ray 28 exiting the compensator 22 by the relation:

$$\Psi(\vec{r}^1) = \Psi_0(\phi,\theta) e^{-\int \frac{\mu}{\rho}(\vec{r})\rho(\vec{r})\delta(\rho-\hat{r}\cdot\vec{r})d\vec{r}} \left( \frac{SSD^2(\phi,\theta)}{|\vec{r}|^2} \right) \quad (11)$$

where $\Psi_0(\Psi,\theta)$ is the energy fluence for a given ray 28 as described by $\delta(\rho-\hat{r}\cdot\vec{r})$ at the exit of the compensator 22 and serves to define the fluence profile of the compensator and $\theta$ and $\phi$ are the gantry angle and the offset angles of the ray 28 as previously described.

The exponential term represents the attenuation of the ray 28 from the exit of the compensator 22 to the voxel $\vec{r}$ caused by the mass of the patient 17 where by $\mu/\rho(\vec{r}^1)$ is the attenuation for each voxel $\vec{r}$ along the ray 28, $\rho(\vec{r})$ is the density of each voxel $\vec{r}$, SSD ($\phi\theta$) is the distance between the exit of the compensator 22 and the surface of the patient 17, $\hat{r}$ is a unit vector along $\vec{r}$ (where the origin of $\vec{r}$ is now assumed to be the center of rotation of the gantry 45), and $\rho$ is the perpendicular distance from the gantry's center of rotation 45 and the ray 28. The vector is simply a vector along the ray 28 to provide an integration variable.

The fluence at each voxel $\vec{r}$ is related to the fluence of the radiation beam 14 emitted from the compensator 22 by equation (11). In the preferred embodiment, the density and attenuation of each voxel $\vec{r}$, $\mu/\rho(\vec{r})$ and $\rho(\vec{r})$ are assumed to be constant and the fan beam of radiation is approximated by a parallel beam, hence $$\frac{SSD^2(\phi,\theta)}{|\vec{r}|^2} = 1$$

Borrowing from the mathematics of tomographic image reconstruction, the fluence map 86 may be "reverse" back projected (i.e. projected) by projector 85 to determine a fluence profile to be produced by the external-source necessary to generate the desired fluence map and hence dose.

This projection is simply the opposite of a typical back projection used to form an image of a tomographic slice of a patient 17 from a series of projections taken in a tomographic imaging system. Because a projection is a line integral across a distribution, the energy fluence distribution for each voxel (equation (11)) is first differentiated with respect to the rayline $\vec{t}$:

$$\frac{d\Psi(\vec{r})}{dt} = \left[ \frac{\mu}{\rho}(\vec{r})\rho(\vec{r})\delta(\rho-\hat{r}\cdot\vec{r}) + \frac{2}{t} \right] \Psi(\vec{r}) \quad (12)$$

The line integral of $$\frac{d\Psi(\vec{r})}{dt}$$

along $\vec{t}$, corrected for attenuation and inverse-square fall off, then represents the projection operation and $\Psi_0(\Psi,\theta)$ the fluence profile over the offset angles $\phi$ of each gantry angle $\theta$, is:

$$\Psi_0(\phi,\theta) = \int \left[ \frac{\mu}{\phi} \, \vec{(r)}\rho\vec{(r)}\delta(\rho - \hat{r}\cdot\vec{r}) + \frac{2}{t} \right] \times$$

$$(\psi\vec{(r)} \, e^{+\int\mu\rho\vec{(r)}\rho\vec{(r)}\delta(\rho-\hat{r}\cdot\vec{r})d\vec{r}}) \left( \frac{|\vec{r}|^2}{SSD_{(\phi,\theta)}^2} \right) \times \delta(p - \hat{r}\cdot\vec{r})d\vec{t} \quad (13)$$

The projection of equation (13) is represented by projector 85 in FIG. 12.

The projection process, for the purpose of computing fluence profiles for the compensator 22, differs in a fundamental way from the simple inverse of tomographic back projection. The difference is primarily in a concern for the sharpness in the transition of the dose between the irradiated tumorous tissue 68 and the healthy tissue 70. Sharpness in this transition region reduces the irradiation of healthy tissue 70 and is preferred over actual fidelity of the dose to the desired dose map 66.

For this reason, the fluence map 86 from the fluence calculator 84 is prefiltered as shown by process block 88 to produce a filtered fluence map $\Psi''$ $(\phi,\theta)$ as follows:

$$\Psi''(\phi,\theta) = F^{-1}\{F\{\Psi(\phi,\theta)|\omega|\}_+ \quad (14)$$

where $\Psi(\phi,\theta)$ is the fluence map 86 and $|\omega|$ is a ramp filter in frequency space and the '+' subscript indicates the positive component of the filtering result. This prefilter 88 serves to increase the high frequency content of the fluence map 86 and thus to aid in rapid transition of dose at the tumor/non-tumor interface.

It is noted that this prefilter 88 is similar to the filter used in tomographic imaging's "filtered" back projection. That is, like tomographic imaging, the filter de-emphasizes the low frequency components of the projection in producing image data. In addition other prefilters may be applied to correct for the use of the radially symmetric kernel (equation (6)) in computing the dose map from the terma map composed from the fluence profile.

$\Psi''(\phi,\theta)$ will be termed the "desired fluence profile and refer to the desired profile of the radiation beam received by the patient.

In practice the computation of a terma map, the generation of a fluence map and the calculation of the fluence profiles need not be performed as discrete steps but may be accomplished by a direct projection of the dose map with appropriate filtering. The filtering is accomplished by a "fast inversion filter" which combines in projection space the operation of deconvolution and ramp filtration.

This may be symbolically specified by the following equation $$\Psi(\phi,\theta) = \rho, \{D(\vec{r})\} \otimes I(t) \quad (15)$$

where $\rho$ refers to a projection operation and $I(t)$ is the fast inversion filter. The $\otimes$ operators refers to a convolution operation such as would normally be done in Fourier space using a fast Fourier transformation.

Referring still to FIG. 12 the fluence profile calculations of block 78, including the deconvolver 80, the fluence calculator 84, the prefilter 88 which includes any projection space filter (such as a ramp filter, a fast inversion filter followed by truncation of zeros), and the projector 85 thus produce fluence profiles which together create an estimated treatment sinogram 87' from the desired dose map 66. The fluence profile calculator 78 may use the Fourier convolution of equation (9) in the estimate of the fluence profiles at this stage, accepting minor inaccuracies in that process, to be corrected at a later stage, as will be described below.

4. Iteration

Figure 13:
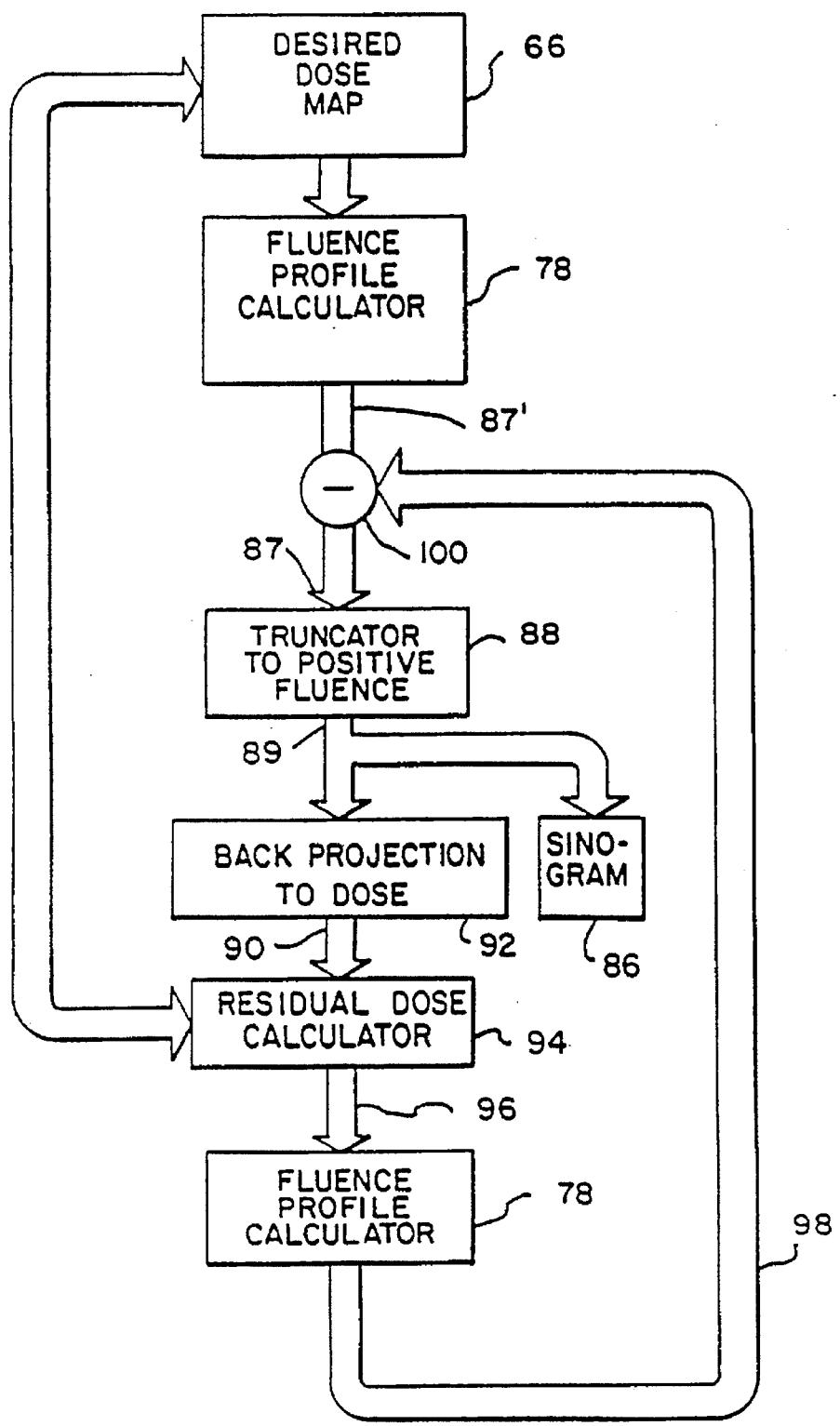
FIG. 13 is a block diagram depicting the overall iterative method of controlling the compensator of the present invention, employing the fluence profile calculation method of FIG. 12.

Referring now to FIG. 13, the fluence profile calculator 78 converts the desired dose map 66 to an estimated treatment sinogram 87', however the fluence profiles of this estimated treatment sinogram 87' may not be used to control the compensator 22 because, in general, the estimated treatment sinogram 87 will include positive and negative values of fluence. Only positive values of fluence are physically realizable by the compensator 22; a negative value of fluence would represent a ray 28 that absorbed radiation along its path which is physically unrealizable.

Accordingly, at process block 88, the fluence values of the estimated treatment sinogram 87' are truncated to positive fluence values 89. As a result of this truncation, the estimated treatment sinogram 87' no longer produces the desired dose map.

The amount of error resulting from the truncation producing the positive fluence profiles 89 is determined by back projecting the positive fluence values 89 to an actual dose map 90 deviating from the desired dose map 66. This back projection is accomplished by computing a fluence map from the positive fluence values 89 per equation (11) and a terma map per equation (4) and then convolving the terma map with the kernel per equation (7) to establish the actual dose map 90 per process block 92 of FIG. 13.

In this back projection, the assumption of spatial invariance of the convolution kernel $B(\vec{r}-\vec{r}^1)$ is not made so as to produce a more accurate actual dose map 90.

The projection of a fluence profile onto a patient 17 to compute a dose map may be performed by a number of other procedures known to those of ordinary skill in the art.

The actual dose map 90 is compared to the desired dose map 66 to produce residual dose map 96 as indicated by process block 94. In the preferred embodiment, the comparison subtracts from the values of each voxel $\vec{r}$ of the actual dose map 90, the greater of: a) the corresponding value of desired dose map 66, or b) a predetermined upper dose constraint. The predetermined upper dose constraint is a threshold number that is deemed an acceptable dose to tumorous tissue 68. Clearly, other methods of quantifying the difference between the desired dose map and the actual dose map will be apparent from this description to those of ordinary skill in the art.

Figure 14A:
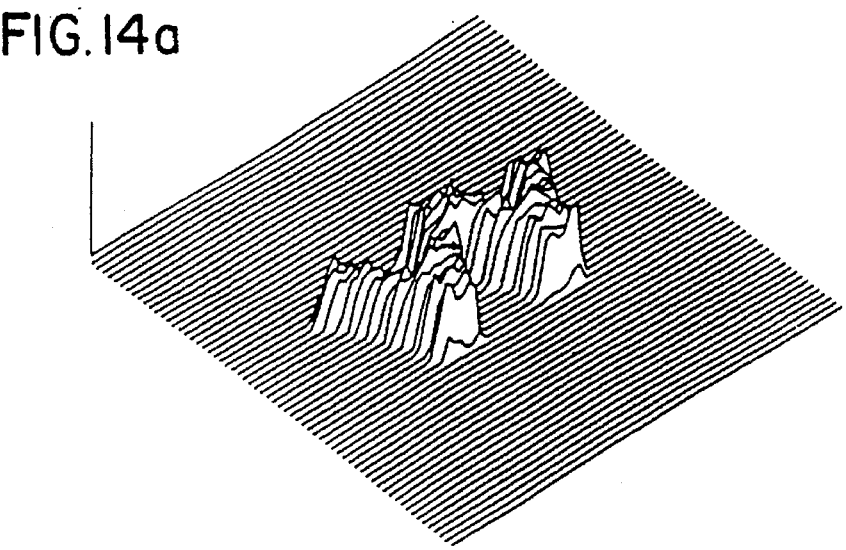
FIGS. 14(a)–(c) are perspective views of plots showing the error between the desired dose distribution and the actual dose distribution obtained with the present invention for one, two and four steps of iteration respectively.
Figure 14B:
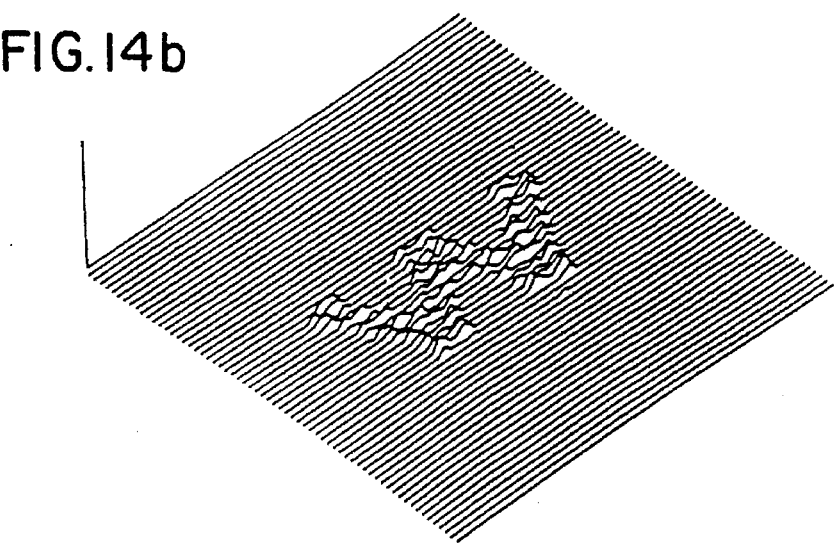
Figure 14C:
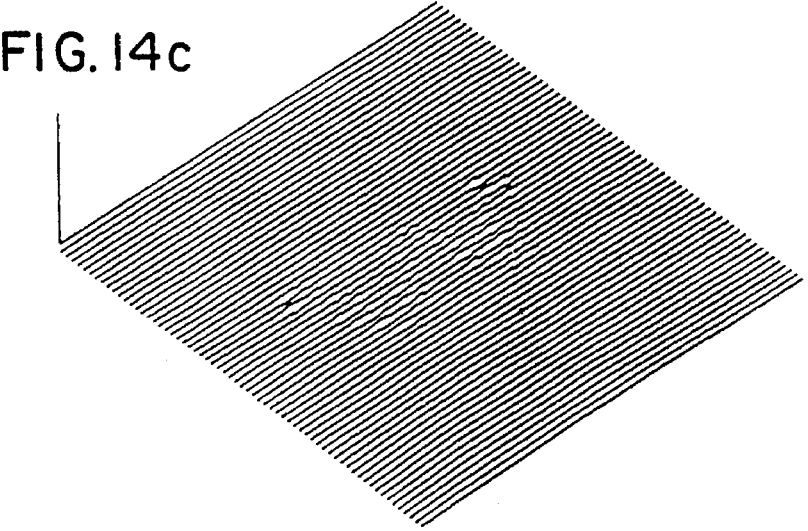

The result of this comparison process 94 is to produce a residual dose map 96 shown in FIG. 14(a). This residual dose map 96 is then, again, operated on by the fluence profile calculator 78 (in lieu of the desired dose map 66) to produce an error fluence profile 98 (in lieu of the estimated treatment sinogram 87).

A thus produced error fluence profile 98 is subtracted by subtracter 100 from the estimated treatment sinogram 87' to produce a new estimated treatment sinogram 87.

As shown in FIG. 13, this new estimated treatment sinogram 87 is repeatedly operated on by process block 88, 92, 94 and 78 for a predetermined number of iterations, the magnitude of the error fluence profile 98 values decreasing with each iteration as shown in FIGS. 13(b)–(d) until a suitably low error fluence profile 98 is obtained.

The new estimated fluence profile 87 is then truncated per process block 88 to produce a final fluence profile sinogram 91.

Figure 8C:
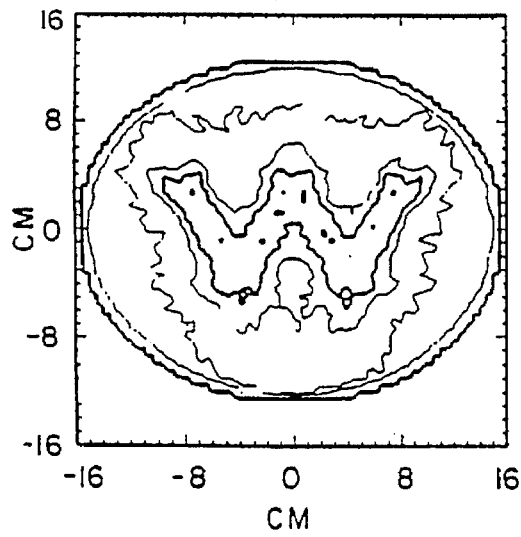
Figure 8D:
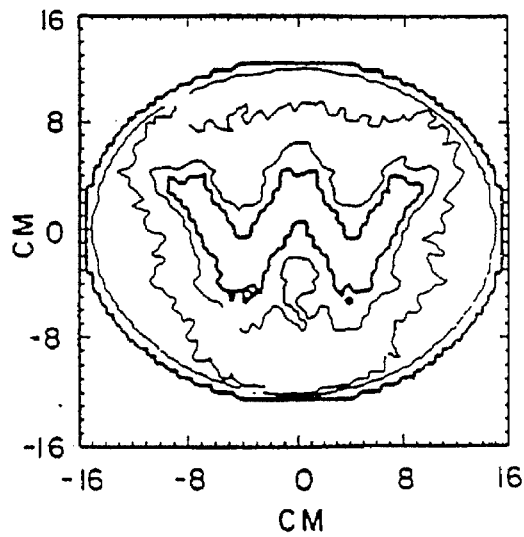

Referring again to FIGS. 8(b), (c) and (d), dose maps obtained by the present invention corresponding to a desired dose map 66 of FIG. 8(a) are shown after: one iteration (FIG. 8(b)); two iterations (FIG. 8(c)); and ten iterations (FIG. 8(d)). The variations in dose in the target volume shown in FIG. 8(d) are plus or minus 2% about the predetermined upper limit of 1,000 cGy.

Figure 15A:
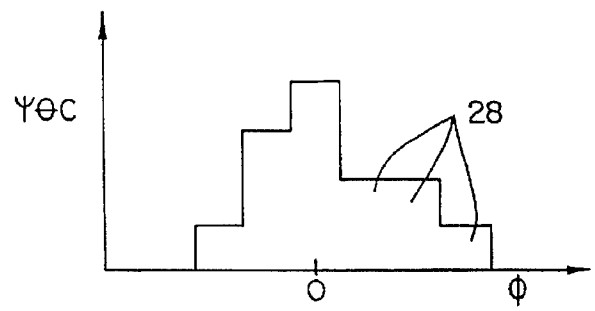
FIGS. 15(a)–(b) represent simplified fluence profiles where
Figure 15B:
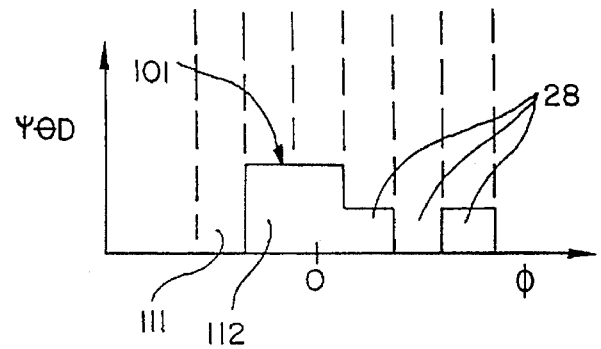

5. Creating An Attenuation Profile From The Source Profile and Desired Profile As described above, the source profile 100 can be obtained by running a test in which substantially no mass is placed within the space between the radiation source 12 and the detector array 50'. Referring to FIG. 15(a), a simplified source profile 100 includes six separate rays 28 each having a different value of fluence $\Psi(\theta,\phi)_s$ generally being higher for the center rays per the profile 100 of FIG. 3(a). These rays 28 must be attenuated to attain a desired profile 101 of FIG. 15(b). The desired profile 101 may require rays 111 having no intensity and attenuated rays 112 in other areas.

Knowing the desired profile 101 and the source profile 100, a dose calculator 104 can generate a fraction of open time within the duty cycle for each leaf 30 necessary to modify the source profile 100 to produce the desired profile 101 as follows:

$$\text{Open Fraction of Duty Cycle }(\phi,\theta) = 1 - \left( \frac{\Psi(\phi,\theta)_S - \Psi(\phi,\theta)_D}{\Psi(\phi,\theta)_S} \right) \quad (16)$$

Where $\Psi(\phi,\theta)_S$ refers to the fluence of one ray of the source profile 100, $\Psi(\phi,\theta)$ D refers to the fluence of the corresponding ray of the desired profile 101 where $\Psi(\phi,\theta)_D \leq \Psi(\phi,\theta)_S$. $\theta$ and $\phi$ are the gantry angle and the offset angles of the ray 28 (each leaf 30 being associated with one ray 28).

Referring to FIG. 7, a controller 104 combines the duty cycles for all of the leaves 30 at a given gantry angle $\theta$ to produce an attenuation profile 105 for the gantry angle $\theta$. The attenuation profile 105 can then be stored in the mass storage unit 64 and called upon later to direct the movement of the compensator leaves 30. When the attenuation profiles 105 are used, the non-uniform source profile is accounted for during irradiation and the full radiation capability of the radiation source 12 is used.

IV. The Second Embodiment Of The Radiation Source

Figure 17:
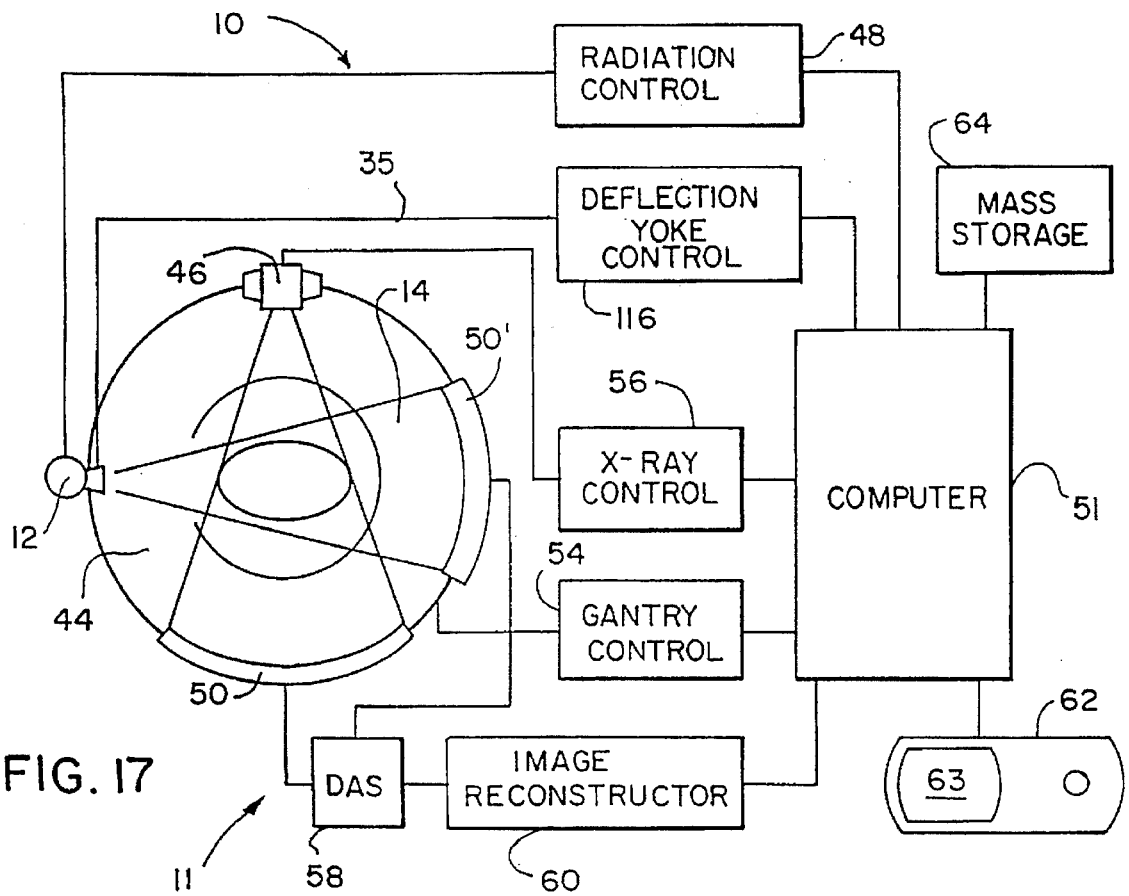
FIG. 17 is a block diagram similar to FIG. 6 showing the elements of a radiation therapy apparatus used in a second embodiment of the present invention.

Referring again to FIGS. 6 and 17, the hardware configurations of the first and second embodiments of the present invention are substantially the same. The only difference between the two configurations is that the collimator control 52 in FIG. 6 is replaced by a deflection yoke control 116 in FIG. 17 and the collimator 22 in FIG. 6 is replaced by a deflection yoke inside the radiation source 12 in FIG. 17.

Referring to FIG. 16, a radiation therapy compensator constructed in accordance with a second embodiment of the present invention has a linac 1 producing an electron stream 6 that is redirected by an achromatic bending magnet 106 toward a target 2. Among the parts unique to the second embodiment is a deflection yoke 108 disposed along the electron path between the linac 1 and the target 2.

The yoke 108 consists of a non-achromatic bending magnet 111 capable of varying the field within its magnetic passageway 112. Electrons 6 accelerated by the linac 1 pass through the magnetic passageway 112 prior to impacting the target 2. By changing the field strength within the magnetic passageway 112, the electron stream 6 can be deflected within a single plane so that the stream 6 impacts the target 2 at different positions along an impact line 120 rather than at a single point. The non-achromatic yoke 108 may oscillate the electron stream 6 along a plane of oscillation 109. During such oscillation, the source profile 113 moves with the point of impact of the electrons and target 2.

Figure 18:
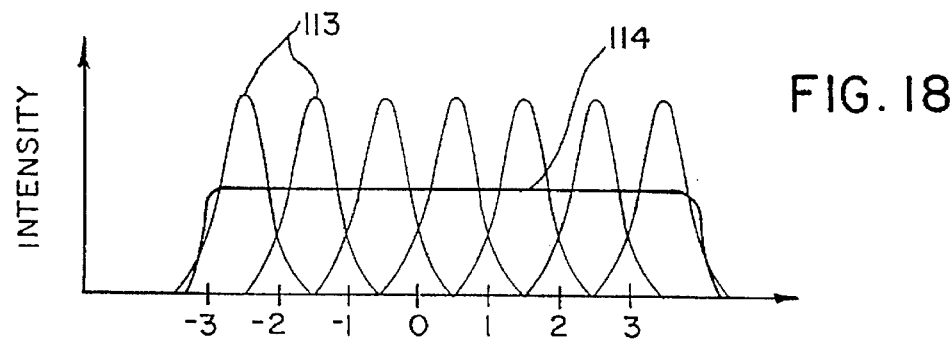
FIG. 18 is a graphical representation showing the source fluence profile in a plurality of positions as it is swept through a plane of oscillation to produce an averaged uniform profile.

Referring to FIG. 18, by oscillating a non-uniform source profile 113 across a wide field, the resulting intensity across the field can effectively be made uniform as the multiple non-uniform source profiles 113 are averaged, thereby, forming a uniform average profile 114. It should be recognized that irregularities in the source profile 113 need not be known because they are averaged into the uniform average profile 114. It should also be recognized that relatively wide uniform radiation fields can be generated.

In operation, prior to a therapy session, a test can be run in which no mass is placed between the radiation source 12 and the detectors 50' thereby generating a uniform average profile 114 for therapy planning purposes.

The above description has been that of two embodiments of the present invention. It will occur to those who practice the art that many modifications may be made without departing from the spirit and scope of the invention.

For example, the fluence profile calculator 78 that is part of the therapy planning software could be used instead of the dose calculator 102 to take into account the non-uniform source profile to generate an attenuation profile for each gantry angle $\theta$ weighted to compensate the non-uniform field of the source fluence. In this manner the duty cycle calculation (Equation. 16) could be worked into the fluence calculation at an earlier stage.

It should also be understood that both embodiments may be used together to achieve a controllable "wide" fan beam field. As seen in FIG. 16, the non-achromatic yoke 108 can be placed between the achromatic bending magnet 106 and the compensator 22. The yoke 108 can produce a wide, uniform field with little loss of energy while the compensator 22 may control the intensity of individual rays within the wide field. In the alternative, the compensators can be used together, one controlling a first dimension of the field and the other perpendicular thereto controlling the second dimension. For example, the non-achromatic yoke 108 could flatten the field along field thickness while the compensator 22 compensates the field along the field width. Further, it is not imperative that the first embodiment be used with a linear accelerator. The compensator 22 may operate in conjunction with any radiation producing source.

Further, by varying the sweep speed of the electron beam of the linac, the fluence of the rays 28 may be controlled to augment or eliminate the need for the compensator 22. In order to apprise the public of the various embodiments that may fall within the scope of the invention, the following claims are made:

We claim:

1. In a radiation therapy machine having a radiation source for producing a radiation beam directed toward a patient at a plurality of treatment angles, the beam including a plurality of adjacent rays spaced about one central ray, each ray having an energy fluence, the energy fluences together forming a non-uniform source fluence profile, an attenuation apparatus comprising:

a detector positioned within the beam for receiving the beam and determining the non-uniform source fluence profile;

a dose calculator for receiving a desired fluence profile for the patient and the non-uniform source fluence profile and for producing duty cycles indicative of how the non-uniform source profile must be altered to produce the desired fluence profile;

a controller for receiving the duty cycles from the dose calculator and producing an attenuation profile corresponding to each desired fluence profile; and a compensator receiving the attenuation profiles for attenuating rays of the radiation beam to correct the non-uniform source fluence profile of the radiation beam to produce the desired fluence profile.

2. The apparatus as recited in claim 1 wherein the compensator comprises:

a plurality of radiation attenuating leaves;

a supporting structure for guiding the leaves between:
  a closed state centered on the rack within the radiation beam, each leaf thus occluding one ray of the beam;
  an open state with each leaf displaced outside of the radiation beam allowing unobstructed passage of the ray;
motivation means for independently moving each leaf between the open state and the closed state; and
timing means communicating with the motivation means for controlling the ratio of the period of time during which each leaf is in the closed state to the period during which each leaf is in the open state to control the average energy fluence of each ray of the beam.

3. In a radiation therapy machine having a radiation source for producing a fan beam of radiation diverging along a fan beam plane and directed toward a patient, the radiation source comprising:
  a target having substantially similar emission parameters along an impact line defined b the fan beam plane;
  an electron generator to produce a stream of electrons directed at the target, the electrons impacting the target and producing a plurality of beam rays diverging about one central ray in the fan beam plane, the fluence of the diverging rays describing a non-uniform fluence profile; and
  an electron deflecting means positioned between the electron source and the target to continuously move the electron stream back and forth along the impact line during irradiation so that the electron stream impacts the target at different positions along the fan beam plane to produce beam rays having a substantially uniform average fluence.

4. The machine as recited in claim 3 wherein the electron deflecting means comprises a bending magnet which magnetically oscillates the electron stream.

5. The therapy machine as recited in claim 3 wherein the target is tungsten.

* * * * *

UNITED STATES PATENT AND TRADEMARK OFFICE
CERTIFICATE OF CORRECTION

PATENT NO. : 5,625,663
DATED : April 29, 1997
INVENTOR(S) : Swerdloff et al.

It is certified that error appears in the above-identified patent and that said Letters Patent is hereby corrected as shown below:

The Abstract should read:

A radiation therapy apparatus includes a compensator having a plurality of leaves to divide a radiation beam into rays each of which may be effectively and individually attenuated over a range of attenuations by controlling the ratio of time in which each leaf is in the open and closed states. The compensator is used to compensate for the non-uniform source fluence profile of the radiation beam. In a second embodiment, a radiation therapy apparatus includes a an oscillating means for oscillating an electron stream along a line on a radiation generating target so that the resulting field of radiation emanating from the target within the plane of oscillation is uniform over time. The invention eliminates the need for beam flattening filters and thus more effectively uses the energy of the radiation beam.

UNITED STATES PATENT AND TRADEMARK OFFICE
CERTIFICATE OF CORRECTION

PATENT NO. : 5,625,663
DATED : April 29, 1997
INVENTOR(S) : Swerdloff et al.

It is certified that error appears in the above-identified patent and that said Letters Patent is hereby corrected as shown below:

Col. 8, line 31, "angle 8"  Should be --angle $\theta$--

Col. 9, lines 22, 29, 31, 34, 39, 42, 46, 51, 57, 59, 61, 62, 66,
Col. 10, lines 1, 2, 8, 12, 14, 17, 20, 24, 27, 35, 46, 50, 54, 59, 61,
Col. 11, lines 37, 42, 53, 58, 60, Col. 12, lines 8, 19
"$\vec{r}^{1}$"  Should be --$\vec{r}'$--

Col. 12, line 11, " $\Psi_0(\Psi,\theta)$  Should be -- $\Psi_0(\phi,\theta)$ --.

Col. 12, line 25, "$\vec{r}$"  Should be --$\hat{r}$--

Col. 15, line 22, " $\Psi(\phi,\theta)D$  Should be --$\Psi(\phi,\theta)_D$--

UNITED STATES PATENT AND TRADEMARK OFFICE
CERTIFICATE OF CORRECTION

PATENT NO. : 5,625,663
DATED : April 29, 1997
INVENTOR(S) : Swerdloff, et al

It is certified that error appears in the above-identified patent and that said Letters Patent is hereby corrected as shown below:

Claim 3, line 19, "defined b the fan beam"  Should be -- defined by the fan beam --

Signed and Sealed this

Third Day of March, 1998

Attest:

BRUCE LEHMAN

Attesting Officer    Commissioner of Patents and Trademarks